(12) United States Patent
Wei et al.

(10) Patent No.: US 6,989,254 B2
(45) Date of Patent: Jan. 24, 2006

(54) DIRECT ENCAPSULATION OF BIOMACROMOLECULES IN SURFACTANT TEMPLATED MESOPOROUS AND NANOPOROUS MATERIALS

(75) Inventors: Yen Wei, Plainsboro, NJ (US); Jigeng Xu, Philadelphia, PA (US); Hua Dong, Philadelphia, PA (US); Qiuwei Feng, Morrisville, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 10/332,423

(22) PCT Filed: Jul. 31, 2001

(86) PCT No.: PCT/US01/23979

§ 371 (c)(1),
(2), (4) Date: Jul. 10, 2003

(87) PCT Pub. No.: WO02/10218

PCT Pub. Date: Feb. 7, 2002

(65) Prior Publication Data

US 2004/0014189 A1    Jan. 22, 2004

Related U.S. Application Data

(60) Provisional application No. 60/222,266, filed on Jul. 31, 2000.

(51) Int. Cl.
  *C07K 17/14*    (2006.01)
  *C12N 11/14*    (2006.01)
(52) U.S. Cl. .......................... 435/176; 502/62; 530/811
(58) Field of Classification Search ................ 423/338, 423/702; 424/484; 435/176; 502/62; 530/811
  See application file for complete search history.

(56) References Cited

FOREIGN PATENT DOCUMENTS

| WO | WO 99/22227 | 5/1999 |
| WO | WO 99/36357 | 7/1999 |

OTHER PUBLICATIONS

Xu et al., "Use of Poly(Ethylene Oxide) Nonionic Surfactants As Template For Enzyme-Containing Mesoporous Sol-Gel Materials", Polymer Preprints 2000 41(2):1673-1674.

*Primary Examiner*—Jeffrey Edwin Russel
(74) *Attorney, Agent, or Firm*—Licata & Tyrrell P.C.

(57) ABSTRACT

Biomacromolecules encapsulated or immobilized within mesoporous or nanoporous materials via surfactant-templated sol-gel reactions and methods for production of these encapsulated or immobilized biomacromolecules are provided.

2 Claims, No Drawings

DIRECT ENCAPSULATION OF BIOMACROMOLECULES IN SURFACTANT TEMPLATED MESOPOROUS AND NANOPOROUS MATERIALS

This patent application is the U.S. National Stage of International Application No. PCT/US01/23979, filed Jul. 31, 2001, which claims the benefit of priority to U.S. Provisional Application Ser. No. 60/222,266, filed Jul. 31, 2000.

This invention was supported in part by funds from the U.S. government (NIH Grant No.RO1-DE09848) and the U.S. government may therefore have certain rights in the invention.

FIELD OF THE INVENTION

The present invention relates to direct immobilization of enzymes and other bioactive agents to surfactant-templated mesoporous or nanoporous materials. Using significantly modified synthetic conditions, it has now been demonstrated that enzymes encapsulated within mesoporous or nanoporous materials can be obtained via surfactant-templated sol-gel reactions. The encapsulated enzymes exhibit much higher catalytic activity than conventional microporous, materials. Hence, using the present invention enzyme-immobilization can be achieved by surfactant-templated sol-gel synthesis.

BACKGROUND OF THE INVENTION

Encapsulation of enzymes and other biomacromolecules in sol-gel materials has drawn great interest in recent years because of the various potential applications in, for example, biocatalysis, biosensor, and drug release vehicles. Encapsulated enzymes retain the same functionality but usually have higher thermal, storage and operational stability in comparison with their counterparts in solution. However, the apparent activity of an entrapped enzyme is often hindered by internal diffusion, and sometimes, by reduced accessibility in microporous sol-gel matrixes even if the synthesis is optimized to preserve the labile biomolecules.

Recently, chemically inert inorganic oxide sol-gel materials with negligible swelling effects, tunable porosity and high purity have emerged as a new class of host matrixes that are well suited for immobilization of biomolecules under room temperature conditions (Avnir et al. Chem. Mater. 1994, 1605–1614; Yamanaka et al. Chem. Mater. 1992 4:497–500; and Dave et al. Anal. Chem. 1994 66:1120–1127A). Many glucose biosensors based on the entrapment of glucose oxidase or oxidase/peroxidase in sol-gels have been reported (Narang, et al. Anal. Chem. 1994 66:3139–3144; Shtelzer et al. Biotechnol. Appl. Biochem. 1994 19:293–305; and Coche-Guérente et al. Chem. Mater. 1997 9:1348–1352).

Immobilization of bioactive substances in mesoporous, host materials via encapsulation of bioagents through a nonsurfactant-mediated sol-gel reaction is described in WO 99/36357. Using this method, it has been shown that enzymes, such as alkaline phosphatase and horseradish peroxidase, entrapped in the nonsurfactant-templated mesoporous, sol-gel matrixes have significantly higher catalytic activities than those in the nontemplated microporous hosts. One of the reasons for this high bioactivity is that substrate and product molecules can diffuse in and out of the mesoporous host matrixes more easily than in conventional microporous materials of typical pore diameters of less than 2 $\mu$m.

Since 1992, a great number of papers have also been published on surfactant-templated mesoporous or nanoporous materials. Various ionic and nonionic surfactants have been used as the templates in the hydrothermal synthesis of an ordered MCM-41-type of molecular sieve. Mesoporous sol-gel materials, such as the MCM-41 molecular sieves and the like, are among the ideal host matrixes for immobilizing enzymes because of their large pore volumes and controllable pore sizes with narrow distributions appropriate for inclusion compounds. Various synthetic conditions have been used in an attempt to immobilize enzymes in PEO surfactant-templated sol-gel materials, including using different stoichiometric ratios of water to surfactant to silica precursor in the feed (Attard et al. Nature 1995 378:366; Bagshaw et al. Science 1995 269:124215–17; and Zhao et al. J. Am. Chem. Soc. 1998 120:6024). However, due to the harsh conditions used in the hydrothermal synthesis of highly ordered surfactant-templated matrixes such as MCM-41-type molecular sieves most biomacromolecules cannot survive. Previous studies show that near neutral pH and room temperature conditions are generally required for successful sol-gel immobilization of enzymes. Thus, to date, direct immobilization of active biomacromolecules in such materials has been unsuccessful (Diaz et al. Mol. Catal. B: Enzym. 1996 2:115–126).

SUMMARY OF THE INVENTION

An object of the present invention is to provide biomacromolecules encapsulated or immobilized within mesoporous or nanoporous materials via surfactant-templated sol-gel reactions.

Another object of the present invention is to provide a method for encapsulating or immobilizing biomacromolecules in mesoporous or nanoporous materials via surfactant-templated sol-gel reactions conducted at near neutral pH and near room temperature.

DETAILED DESCRIPTION OF THE INVENTION

Using modified synthetic conditions, it has now been demonstrated that surfactant-templated mesoporous and nanoporous materials can serve as host matrixes for immobilizing biomacromolecules.

By "biomacromolecule" it is meant to include any biologically active macromolecule. Examples include, but are not limited to, enzymes, other proteins, cells, organelles and nucleic acids.

Specifically, it has been demonstrated that nonionic surfactant copolymers such as poly(ethylene oxide) (PEO) copolymers can be employed as the template for the synthesis of mesostructured enzyme-containing sol-gel matrixes. The in situ immobilization of horseradish peroxidase (HRP) and glucose oxidase (GOx) in sol-gel materials with PEO templates was successfully carried out under near neutral pH and room temperature conditions. Further, enzymatic assay data show that HRP alone or HRP with GOx in the mesoporous silica or organically modified hybrid silica matrixes have significantly greater enzymatic activities compared to the same enzymes encapsulated in microporous matrixes.

HRP-containing sol-gel materials were synthesized in the presence of various nonionic PEO copolymer surfactants. In the synthesis of HRP-containing sol-gel samples, relatively low ratios of water to surfactant were employed as precipitation was found to occur at higher ratios of 10:1, However, at a weight ratio of $H_2O$ to surfactant of 2:1, the reaction systems were homogeneous at various stages of the sol-gel process from sol to gel. The synthesized HRP-containing sol-gels were mostly homogeneous and transparent or, in some samples, translucent.

The compositions of the PEO surfactant-templated samples are summarized in Table 1. The apparent initial activity ($V_i$) of the sol-gel samples were evaluated at room temperature at $[H_2O_2]=1.0\times10^{-3}$ M (Table 1). The experimental data show that the apparent activities of HRP are quite different among the sol-gel samples templated with different PEO copolymer surfactants under the synthetic conditions used. The sample B78 has an initial specific activity of $V_i=64$ unit $mg^{-1}$ $min^{-1}$, which is about 17% of the specific activity of free HRP (379 unit $mg^{-1}min^{-1}$) assayed under identical conditions. Other samples exhibited relatively lower activities. However, compared to the nontemplated HRP-containing silica or organically modified silica sol-gel materials such as described by Xu et al. (Poly. Prep. (Am. Chem. Soc. Div. Polym. Chem. 2000 41(1), 1042–1043) and Xu et al. (Poly. Prep. Am. Chem. Soc. Div. Polym. Chem. 2000 41(1), 1044–1045), the enzymatic activities of these surfactant-templated sol-gel materials are significantly higher.

TABLE 1

Composition and Activity of HRP-containing Sol-Gels

| Sample Code | Nonionic Surfactant | SiO₂ Calcd | SiO₂ Found | $V_i^d$ unit $mg_{-1}$ $min_{-1}$ | $V_{sp}^c$ $cm^3g^{-1}$ | $S_{BET}^a$ $m^2g^{-1}$ |
|---|---|---|---|---|---|---|
| B30 | BRIJ 30 | 45.8 | 43 | 14 | | |
| B78 | BRIJ 78 | 45.8 | 42 | 64 | 1.02 | 691 |
| DB78 | BRIG 78 | 45.9 | 41 | 39 | 0.99 | 704 |
| L64 | PLURONIC L64 | 45.6 | 42 | 3 | 0.88 | 529 |
| TX100 | TRITON X-100 | 49.7 | 46 | 7 | 0.77 | 613 |
| TX114 | TRITON X-114 | 49.6 | 48 | 15 | | |
| CO890 | IGEPAL CO-890 | 49.8 | 46 | 5 | 0.708 | 567 |

After removing the templates by calcination, the host sol-gel matrixes were characterized by nitrogen adsorption measurements as described by Wei et al. (Adv. Mater. 1998 3:313–316), Wei et al. (Chem. Mater. 1999 11:2023–2029) and Sing et al. (Pure Appl. Chem. 1985 57:603–619). The pore structure parameters of the silica matrixes are summarized in Table 1. The results indicate that the host silica materials are mesoporous with large pore volumes. The pore size distributions are relatively narrow.

The enzymatic activity of the sol-gel samples is believed to be associated, to some extent, with the pore microstructure parameters of the host matrix. As a comparison, the activity of HRP encapsulated in the non-templated microporous sol-gel matrix, prepared in the absence of templates under otherwise identical conditions, was found to be small ($V_i \sim 0.1$ unit $mg^{-1}$ $min^{-1}$; Avnir et al. Chem. Mater. 1994 6:1605–1614; and Dave et al. Anal. Chem. 1994 66:1120A-1127A). The HRP in the nonionic surfactant-templated mesoporous matrixes exhibits remarkable improvements in the enzymatic activity (see Table 1), which could be attributed to the reduced internal diffusion resistance and improved accessibility.

Glucose oxidase is one of the most widely studied enzymes because of its utility in the selective determination of D-glucose, an analyte of broad analytical and pharmaceutical interest. The use of insoluble glucose oxidase provides some advantages that overcome limitations encountered when using soluble enzyme in solution. In particular, use of insoluble glucose results in an increase in the retention of enzyme activity with time and easy separation and recovery with minimum contamination. The insoluble enzyme preparations are ubiquitous in the design of reactor/sensing units and are adaptable to continuous flow sample and reagent processing.

Accordingly, PEO surfactant templates co-immobilized with glucose oxidase (GOx) and horseradish peroxidase (HRP) in silica sol-gel matrixes under near neutral pH conditions were also prepared. The activities of the two enzymes in their catalysis of consecutive reactions, along with structure characterization of the materials were evaluated.

HRP and GOx catalyze, respectively, the two consecutive reactions as illustrated below:

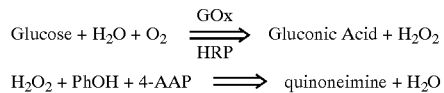

$H_2O_2 + PhOH + 4\text{-}AAP \Longrightarrow$ quinoneimine $+ H_2O$

The change in absorbance of quinoneimine, a red dye, at 510 nm was used to evaluate the enzymatic activity. The relationship between the ratio of HRP/GOx and the activity of free and immobilized HRP/GOx is that the higher the ratio of HRP/GOx, the higher the apparent activity. At higher ratios of HRP/GOx, the product hydrogen peroxide, generated in the GOx catalyzed glucose oxidation, can be consumed more efficiently in the HRP catalyzed reaction. When both GOx and HRP are in solution, there is an increase in the apparent activity, less than 1.5 times at [glucose]=1–400 mM, when the ratio of HRP to GOx is increased from 1 to 10. However, the increase in the activity was more evident, from 2–4 fold at [glucose]=100 mM, when the two enzymes were co-immobilized in sol-gel matrixes. In this case, both HRP and GOx are confined in the interconnected channels of the silica host matrix in which diffusion of the substrate plays a more important role than that in solution. That is, the local concentration of hydrogen peroxide within the sol-gel matrix may be higher than that in homogeneous solution. Furthermore, the results on another set of samples with GOx only entrapped in sol-gel matrixes and assayed with 10 times HRP in solution at [glucose]=100 mM showed a slightly lower activity, i.e., at 85%, when compared to the corresponding samples with both enzymes entrapped.

The dose-response kinetics of immobilized GOx and HRP were measured at [glucose]=1–400 mM. The response time for the surfactant-templated HRP/GOx-containing sol-gel samples was less than 5 minutes, while the nontemplated controls derived from TMOS (control-B) and 95 mol %-TMOS/5 mol %-PhTMS (control-A) had no visible color change for 3 hours after adding glucose.

The activities of free and immobilized HRP/GOx in the pH range of 4.0 to 7.0 were also determined. In these experiments, all the pH values were obtained with 0.10 M phosphate buffer. Although sol-gel entrapped enzymes often exhibited different optimal pH and pH activity profiles, the activity dependence on pH for the immobilized HRP/GOx showed an overall trend similar to that of free HRP/GOx.

It is known that both GOx and HRP are quite stable in a wide range of pH values and temperatures. HRP immobilized in silica sol-gels had similar or even slightly higher apparent activities compared with the same samples without the thermal treatment. In comparison, free GOx, after the thermal treatment, retained only 30% of the apparent activity. Upon immobilization, the HRP/GOx-containing sol-gels (AA 10 and AB 10) exhibited about 80% of the apparent activities in comparison with the samples without thermal treatment.

The $N_2$ sorption results showed that the nontemplated enzyme-containing sol-gel matrixes, i.e., control-A and control-B, were microporous materials. In contrast, the nonionic surfactant-templated HRP/GOx-containing sol-gel samples were mesoporous materials, as evidenced by the nitrogen adsorption isotherms and BJH pore size distributions.

Accordingly, these experiments demonstrate that enzyme immobilization or encapsulation can be achieved by surfactant-templated sol-gel synthesis conducted at near neutral pH and near room temperature. The enzyme-containing sol-gels produced via this method have structural characteristics of mesoporous materials after removing the surfactants and exhibit relatively high remaining enzyme activities. Thus, the template synthesis of the present invention provides a useful means for the in situ immobilization of biomacromolecules in highly ordered mesoporous or nanoporous sol-gel materials or molecular sieves.

As will be understood by one of skill in the art upon reading this disclosure, while the experiments described herein utilized the nonionic surfactant copolymer PEO as the template or pore forming agent, other polyethers or polyamines can be used. The methods disclosed herein are useful with ionic surfactants as well. Examples of ionic surfactants which can be used in the mesoporous or nanoporous templates include, but are not limited to, cationic surfactants such as alkyl and aryl sulfates, zwitter-ionic surfactants containing both cations and anions, and mixtures thereof. Mesoporous or nanoporous materials suitable for encapsulation of biomacromolecules include, but are not limited to, inorganic materials such as silica, aluminosilicates, titania, zirconia, and alumina, organic-modified materials such as alkyl, aryl, and vinyl modified materials, and inorganic, polymer-modified materials such as polymethacrylate and polystyrene.

The following nonlimiting examples are provided to further illustrate the present invention.

EXAMPLES

Example 1

Materials

HRP (EC 1.11.1.7) Type II; 200 purpurogallin units/mg; Sigma, lot 16119522), GOx (E.C. 1.1.3.4, from *Aspergillus niger*; 200 Fluka units/mg), tetramethyl orthosilicate (TMOS), phenyltrimethoxysilane (PhTMS), IGEPAL CO-890 (denoted as surfactant-A), and BRIJ 78 (denoted as surfactant-B) were purchased from Aldrich (Milwaukee, Wis.). 4-Aminoantipyrine (4-AAP), β-D-glucose, phenol (PhOH), and sodium phosphates were supplied by Sigma (St. Louis, Mo.). HCl was from Fisher Scientific (Fair Lawn, N.J.). All chemicals and reagents were used without further purification.

Example 2

Preparation of HRP-Containing Sol-Gels

For the immobilization of HRP (EC 1.11.1.7, Type II; lot 16H9522; Sigma) in silica sol-gel matrixes, the enzyme in buffer solution was added into the prehydrolyzed homogeneous sol of tetramethyl orthosilicate (TMOS, Aldrich) in the presence of nonionic PEO surfactant templates, following modified procedures for the nonsurfactant template synthesis described by Wei et al. (Proc. NAM'99 Tech Prog. North Am. Cataly. Soc. 1999, Boston, Mass., 14), Xu et al. Polym. Prep. (Am. Chem. Soc. Div. Polym. Chem. 2000, 41(1), 1042–1043), Xu et al. Polym. Prep. (Am. Chem. Soc. Div. Polym. Chem. 2000, 41(1), 1046–1047), and Xu et al. Polym. Prep. (Am. Chem. Soc. Div. Polym. Chem. 2000, 41(1), 1044–1045). In a typical preparation for sample B78, 1.45 grams of BRIJ 78 (Aldrich) was mixed with 2.40 grams of distilled $H_2O$ with slight heating. Next, 3.10 grams of TMOS was added to the mixture under magnetic stirring at room temperature. Then, 1.0 mg of HRP (dissolved in 1.0 mL of 10 mM sodium phosphate buffer, pH 7.1) was added to the homogeneous sol under agitation at about 0° C. After gelation, the sample was dried in the air for four days and then in a vacuum oven for three days to afford the enzyme-containing sol-gel. Among the as-synthesized samples using different PEO copolymer surfactants, most of them were transparent or translucent bulk solid, and a few were opaque powder.

Example 3

HRP Activity Assay

A colorimetric method using phenol, 4-aminoantipyrine and hydrogen peroxide ($H_2O_2$) as the dye-generating compounds was used to evaluate the initial activity of HRP, as described in Xu et al. Polym. Prep. (Am. Chem. Soc. Div. Polym. Chem. 2000, 41(1), 1042–1043), Xu et al. Polym. Prep. (Am. Chem. Soc. Div. Polym. Chem. 2000, 41(1), 1046–1047), Xu et al. Polym. Prep. (Am. Chem. Soc. Div. Polym. Chem. 2000, 41(1), 1044–1045), and Worthington, V. (Worthington Enzyme Manual; Worthington Biochemical Co.; Lakewood, N.J. 1993; pp. 293–299).

Example 4

Characterization of HRP-Containing Sol-Gels

The content of $SiO_2$ in as-synthesized sol-gels was estimated from weight loss at 750° C. in the air by thermogravimetric analysis (TGA). The pore structure parameters of sol-gel matrixes after removing surfactants were characterized by nitrogen adsorption measurements on a Micromeritics ASAP 2010 system (Micromeritics, Inc., Norcross, Ga.) at −196° C. Nonionic surfactants were removed from as-synthesized sol-gels by calcination at 600° C. Fine powder from as-synthesized sol-gel samples was heated to 600° C. at a heating rate of 2° C./minute in the air flow and kept at 600° C. for 4 hours before cooling to room temperature. The calcined silica sol-gel material was characterized by the BET method as described by Wei et al. (Adv. Mater. 1993 3:313–316), Wei et al. (Chem. Mater. 1999 11:2023–2029) and Sing et al. (Pure Appl. Chem. 1985 57:603–619).

Example 5

Preparation of Sol-Gel Immobilized HRP/GOx

Two kinds of sols were prepared by acid hydrolysis of pure TMOS (Sol-B) and mixtures of 95 mol % TMOS and 5 mol % PhTMS (Sol-A), respectively, as previously reported (Dong et al. Polym. Prepr. 2000 41(1):602). HRP and GOx were dissolved in 0.010 M phosphate buffer (pH 6.5) in an ice bath at the concentration of 200 unit/mL. Surfactants A and B, each accounting for 50 wt % in the final product, were mixed separately with twice the amount of distilled water and warmed up on a hot plate until homogenous solutions were obtained. Next, each surfactant solution was mixed with either of the above two sols under stirring at room temperature, cooled to 0° C. and, then, mixed with an appropriate amount of HRP and GOx solutions. After gelation, the enzyme-containing gels were dried under room temperature until constant weight was reached. The final enzyme-containing dry gels were ground into fine powders and stored under −15° C. The surfactant-template was extracted from as-synthesized sol-gels with phosphate buffer before the enzymatic activity assay and with EtOH/$H_2O$ (50/50, V/V) before nitrogen sorption measurements. Two control samples (denoted as control-A and control-B) were also prepared in the absence of the templates under otherwise the identical conditions.

Example 6

Assay of HRP/GOx Activity

A calorimetric method, using glucose, phenol and 4-aminoantipyrine as the dye-generating compounds, was used to evaluate the activity of both free and immobilized GOx at room temperature (23° C.) with slight modifications of the protocol described by Worthington, V. (Worthington Enzyme Manual; Worthington Biochemical Co.; Lakewood, N.J., 1993; pp. 293–299). The activity of GOx in the coupling of HRP/GOx was determined from the absorbance change at 510 nm, due to the formation of N-antipyryl-p-benzoquinoneimine, by using a UV-Vis spectrophotometer (Perkin Elmer Lambda 2, Norwalk, Conn.). A Spectronic 20 spectrophotometer (Milton Roy Co.) was also used for some immobilized samples. The samples were first extracted thoroughly with a dilute buffer solution (3×10 mL of 10 mM sodium phosphate buffer solution, pH 6.5, at intervals of 1 hour) before the activity assay. The β-D-glucose aqueous solution was allowed to stand for 24 hours at room temperature before use. 4-AAP was dissolved in phosphate buffer and saturated with $O_2$ by bubbling $O_2$ through for 15 minutes before the activity assay. Thermal stability of GOx was estimated from the remaining activity after thermal treatment at 60° C. for 30 minutes, in comparison with the activity of the same samples without the treatment. The thermally treated samples were assayed with [glucose]=100 mM at pH=6.5.

What is claimed is:

1. A biomacromolecule encapsulated or immobilized within a highly ordered mesoporous or nanoporous material with narrow pore size distribution produced via a surfactant-templated sol-gel reaction conducted at near neutral pH and near room temperature.

2. A method for producing encapsulated or immobilized biomacromolecules in mesoporous or nanoporous materials comprising:
    conducting a surfactant-templated sol-gel reaction with the biomacromolecule at near neutral pH and near room temperature; and
    removing the surfactants to produce a biomacromolecule-containing sol-gel having structural characteristics of a mesoporous or nanoporous material.

* * * * *